United States Patent
Thornberry (10) Patent No.: US 9,539,112 B2
(45) Date of Patent: Jan. 10, 2017

(54) COMPUTER-GUIDED SYSTEM FOR ORIENTING A PROSTHETIC ACETABULAR CUP IN THE ACETABULUM DURING TOTAL HIP REPLACEMENT SURGERY

(71) Applicant: Robert L. Thornberry, Tallahassee, FL (US)

(72) Inventor: Robert L. Thornberry, Tallahassee, FL (US)

( * ) Notice: Subject to any disclaimer, the term of this patent is extended or adjusted under 35 U.S.C. 154(b) by 486 days.

(21) Appl. No.: 13/852,829

(22) Filed: Mar. 28, 2013

(65) Prior Publication Data

US 2013/0261633 A1 Oct. 3, 2013

Related U.S. Application Data

(60) Provisional application No. 61/616,939, filed on Mar. 28, 2012.

(51) Int. Cl.
*A61F 2/46* (2006.01)

(52) U.S. Cl.
CPC ............. *A61F 2/4609* (2013.01); *A61B 34/20* (2016.02); *A61B 34/10* (2016.02); *A61B 2034/2048* (2016.02); *A61B 2034/2063* (2016.02)

(58) Field of Classification Search
CPC ........ A61F 2/46; A61F 2/4603; A61F 2/4609; A61F 2002/4623; A61F 2002/4681; A61B 2034/2048; A61B 2034/2063
See application file for complete search history.

(56) References Cited

U.S. PATENT DOCUMENTS

| 3,868,103 | A | * | 2/1975 | Pageot ................... | A61G 13/02 137/596 |
| 6,033,415 | A | | 3/2000 | Mittelstadt et al. | |
| 6,205,411 | B1 | * | 3/2001 | DiGioia, III .......... | A61B 17/15 623/901 |
| 6,322,565 | B1 | | 11/2001 | Garner et al. | |
| 6,385,475 | B1 | * | 5/2002 | Cinquin ................. | A61B 5/107 128/920 |

(Continued)

FOREIGN PATENT DOCUMENTS

WO    WO 2011/106861    9/2011

OTHER PUBLICATIONS

Aesculap Orthopaedics, OrthoPilot, Brochure, 2008.
(Continued)

*Primary Examiner* — Christian Sevilla
*Assistant Examiner* — Eric S Gibson
(74) *Attorney, Agent, or Firm* — Pandiscio & Pandiscio (57) ABSTRACT

A computer-guided system for orienting an insert during a surgical procedure, the computer-guided system comprising:
 a surgical table for supporting a patient, the surgical table being capable of movement about three axes;
 a table inertial measurement unit for measuring movement of the surgical table;
 a patient inertial measurement unit for measuring movement of the patient;
 an insert inertial measurement unit for measuring movement of the insert; and
 computational means for determining the relative positioning of the patient and the insert based upon movement of the surgical table, movement of the patient, and movement of the insert.

20 Claims, 7 Drawing Sheets

(56) References Cited

U.S. PATENT DOCUMENTS

| | | | |
|---|---|---|---|
| 6,607,487 B2* | 8/2003 | Chang | A61B 8/4281 600/437 |
| 6,723,102 B2 | 4/2004 | Johnson et al. | |
| 6,877,239 B2* | 4/2005 | Leitner | A61B 19/52 33/511 |
| 7,313,430 B2 | 12/2007 | Urquhart et al. | |
| 7,559,931 B2 | 7/2009 | Stone | |
| 7,780,681 B2* | 8/2010 | Sarin | A61B 5/103 606/102 |
| 8,000,926 B2* | 8/2011 | Roche | A61B 19/5244 702/150 |
| 8,057,479 B2 | 11/2011 | Stone | |
| 8,057,482 B2 | 11/2011 | Stone et al. | |
| 8,118,815 B2 | 2/2012 | van der Walt | |
| 8,287,522 B2 | 10/2012 | Moses et al. | |
| 8,336,220 B2 | 12/2012 | Eaton et al. | |
| 8,391,954 B2 | 3/2013 | Quaid, III | |
| 8,400,312 B2* | 3/2013 | Hotokebuchi | A61B 5/06 340/539.12 |
| 8,494,825 B2 | 7/2013 | Thornberry | |
| 8,786,680 B2* | 7/2014 | Shiratori | G06F 3/011 345/156 |
| 8,888,786 B2* | 11/2014 | Stone | A61B 17/175 600/587 |
| 8,951,256 B2* | 2/2015 | Burroughs | A61B 6/0421 606/86 R |
| 8,961,526 B2* | 2/2015 | Burroughs | A61B 19/5244 606/86 R |
| 2002/0038307 A1 | 3/2002 | Obradovic et al. | |
| 2002/0099288 A1* | 7/2002 | Chang | A61B 8/4281 600/439 |
| 2003/0153829 A1 | 8/2003 | Sarin | A61B 5/103 600/426 |
| 2004/0087852 A1* | 5/2004 | Chen | A61B 6/547 600/407 |
| 2004/0152970 A1* | 8/2004 | Hunter | A61B 17/15 600/424 |
| 2004/0152972 A1* | 8/2004 | Hunter | A61B 17/15 600/424 |
| 2004/0153079 A1 | 8/2004 | Tsougarakis et al. | |
| 2004/0210233 A1* | 10/2004 | Yoon | A61B 19/46 606/102 |
| 2004/0230199 A1 | 11/2004 | Jansen et al. | |
| 2004/0243148 A1* | 12/2004 | Wasielewski | A61B 17/00 606/130 |
| 2005/0085822 A1 | 4/2005 | Thornberry et al. | |
| 2005/0119639 A1 | 6/2005 | McCombs et al. | |
| 2005/0240275 A1 | 10/2005 | Chappuis | |
| 2006/0074289 A1* | 4/2006 | Adler | A61B 5/065 600/407 |
| 2006/0142656 A1* | 6/2006 | Malackowski | A61B 17/1626 600/424 |
| 2006/0142657 A1 | 6/2006 | Quaid et al. | |
| 2007/0211022 A1* | 9/2007 | Boillot | G06F 3/0325 345/156 |
| 2007/0260253 A1 | 11/2007 | Johnson et al. | |
| 2007/0276394 A1 | 11/2007 | Johnson et al. | |
| 2007/0287911 A1* | 12/2007 | Haid | A61B 19/52 600/429 |
| 2008/0004633 A1 | 1/2008 | Arata et al. | |
| 2008/0039716 A1 | 2/2008 | Tuma | |
| 2008/0051910 A1* | 2/2008 | Kammerzell | A61B 19/52 623/22.21 |
| 2008/0058835 A1 | 3/2008 | Farritor et al. | |
| 2008/0269596 A1* | 10/2008 | Revie | A61B 6/12 600/424 |
| 2009/0138019 A1 | 5/2009 | Wasielewski | |
| 2009/0171370 A1* | 7/2009 | Yoon | A61F 2/4609 606/130 |
| 2009/0289806 A1 | 11/2009 | Thornberry | |
| 2009/0306509 A1* | 12/2009 | Pedersen | G01S 15/8936 600/446 |
| 2009/0318930 A1 | 12/2009 | Stone et al. | |
| 2010/0064216 A1 | 3/2010 | Borja et al. | |
| 2010/0076505 A1* | 3/2010 | Borja | A61F 2/4657 606/86 R |
| 2010/0127879 A1* | 5/2010 | Hotokebuchi | A61B 5/06 340/573.7 |
| 2010/0137871 A1 | 6/2010 | Borja | |
| 2010/0249657 A1* | 9/2010 | Nycz | A61B 19/46 600/587 |
| 2011/0093086 A1* | 4/2011 | Witt | A61F 2/3609 623/22.15 |
| 2011/0166435 A1 | 7/2011 | Lye | |
| 2011/0190629 A1* | 8/2011 | Guenther | A61B 8/08 600/437 |
| 2011/0190775 A1 | 8/2011 | Ure | |
| 2011/0218458 A1* | 9/2011 | Valin | A61B 19/5244 600/595 |
| 2011/0257653 A1* | 10/2011 | Hughes | A61B 19/50 606/79 |
| 2011/0275957 A1* | 11/2011 | Bhandari | A61B 5/1114 600/595 |
| 2012/0022406 A1* | 1/2012 | Hladio | A61F 2/4609 600/587 |
| 2012/0130279 A1 | 5/2012 | Stone | |
| 2012/0136402 A1* | 5/2012 | Burroughs | A61B 6/0421 606/86 R |
| 2012/0143268 A1* | 6/2012 | Burroughs | A61B 19/5244 606/86 R |
| 2012/0157887 A1* | 6/2012 | Fanson | A61B 19/5244 600/595 |
| 2012/0203140 A1* | 8/2012 | Malchau | A61B 5/1114 600/595 |
| 2012/0323247 A1* | 12/2012 | Bettenga | A61F 2/46 606/91 |
| 2012/0327194 A1* | 12/2012 | Shiratori | G06F 3/011 348/47 |
| 2013/0053859 A1* | 2/2013 | Penenberg | A61B 17/164 606/91 |
| 2013/0150863 A1* | 6/2013 | Baumgartner | A61B 17/8866 606/102 |
| 2013/0158476 A1* | 6/2013 | Olson | A61B 5/7285 604/95.01 |
| 2013/0231672 A1* | 9/2013 | Paradis | A61F 2/4657 606/91 |
| 2013/0261633 A1* | 10/2013 | Thornberry | A61F 2/4609 606/91 |
| 2014/0005531 A1* | 1/2014 | Taylor | A61B 19/5244 600/424 |
| 2014/0031722 A1* | 1/2014 | Li | A61F 2/4609 600/587 |
| 2014/0052149 A1* | 2/2014 | van der Walt | A61B 19/20 606/130 |
| 2014/0114179 A1* | 4/2014 | Muller | A61B 19/5244 600/424 |
| 2014/0135616 A1* | 5/2014 | Stein | G06F 19/3406 600/424 |
| 2014/0135773 A1* | 5/2014 | Stein | G06F 19/3406 606/80 |
| 2014/0135791 A1* | 5/2014 | Nikou | A61B 19/2203 606/130 |
| 2014/0142864 A1* | 5/2014 | Spears | A61B 5/1112 702/19 |
| 2014/0303631 A1* | 10/2014 | Thornberry | A61F 2/4609 606/91 |
| 2014/0336660 A1* | 11/2014 | Gibson | A61F 2/4609 606/91 |
| 2014/0378828 A1* | 12/2014 | Penenberg | A61F 2/4657 600/424 |
| 2015/0182350 A1* | 7/2015 | Behzadi | A61F 2/4609 606/91 |
| 2015/0182351 A1* | 7/2015 | Behzadi | A61B 17/3468 606/91 |
| 2016/0038161 A1* | 2/2016 | Gibson | A61B 17/1746 606/91 |
| 2016/0038307 A1* | 2/2016 | Bettenga | A61F 2/46 606/91 |

(56) References Cited

U.S. PATENT DOCUMENTS

OTHER PUBLICATIONS

Bozic, Kevin J. et al., Epidemiology of Revision Total Hip Arthroplasty in the United States, The Journal of Bone and Joint Surgery, 2009, pp. 128-133, vol. 91-A, No. 1.
Digioia, Anthony M. et al., An Image Guided Navigation System for Accurate Alignment in Total Hip Replacement Surgery, 1998, Carnegie Mellon University and Shadyside Hospital.
Ghandi, Rajiv et al., Computer navigation in total hip replacement: a meta-analysis, International Orthopaedics, 2009.
Mako Surgical Corp., MAKOplasty Defines Confidence in THA Outcomes Robotic Arm Accuracy Combined with Advanced Implant Performance, Brochure, 2012.
Malik, Aamar et al., Impingement with Total Hip Replacement, The Journal of Bone and Joint Surgery, Aug. 2007, vol. 89-A, No. 8.
Manzottl, Alfonso et al., Does computer-assisted surgery benefit leg length restoration in total hip replacement? Navigation versus conventional freehand, International Orthopaedics, vol. 35, Issue 1, 2011.
Medtronic, Inc., StealthStation S7 System, Brochure, 2013.
Orthoalign, OrthoAlign precise alignment technology, Brochure, 2015.
Slover, James D., Impact of Hospital Volume on the Economic Value of Computer Navigation for Total Knee Replacement, The Journal of Bone and Joint Surgery, Jul. 2008, vol. 90-A, No. 7.
Spencer, J. M. F. et al., Computer navigation of the acetabular component A Cadaver Reliability Study, The Journal of Bone and Joint Surgery, Jul. 2008, vol. 88-B, No. 7.
Stein, David et al., Theory, Design, and Implementation of a Spherical Encoder, Proceedings of the 2001 IEEE International Conference on Robotics & Automation, 2001.
Angadji et al., Influence of Cup Orientation on the Wear Performance of Metal-on-Metal Hip Replacements, Proceedings of the Institution of Mechanical Engineers, Part H: Journal of Engineering in Medicine, 2009, vol. 223, pp. 449-457.
Bozic et al., The Epidemiology of Bearing Surface Usage in Total Hip Arthroplasty in the United States, The Journal of Bone and Joint Surgery, 2009, vol. 91-A, No. 7, pp. 1614-1620.
Digioia III et al., Surgical Navigation for Total Hip Replacement with the Use of HIPNAV, Operative Techniques in Orthopaedics, 2000, vol. 10, No. 1, pp. 3-12.
Ecker et al., Application of Surgical Navigation to Total Hip Arthroplasty, Proceedings of the Institution of Mechanical Engineers, Part H: Journal of Engineering in Medicine, 2007, vol. 221, pp. 699-712.
Gofton et al., The Effect of Computer Navigation on Trainee Learning of Surgical Skills, The Journal of Bone and Joint Surgery, 2007, vol. 89-A, No. 12, pp. 2819-2827.
"iNstride Hip Navigation", Stryker website, http://www.stryker.com/en-us/products/Orthopaedics/ComputerAsssted Surgery/HipNavigationSurgery/iNstride/index.htm.
Iorio et al., Orthopedic Surgeon Workforce and Volume Assessment for Total Hip and Knee Replacement in the United States: Preparing for an Epidemic, The Journal of Bone and Joint Surgery, 2008, vol. 90-A, No. 7, pp. 1598-1605.
Kurtz et al., Future Clinical and Economic Impact of Revision Total Hip and Knee Arthroplasty, The Journal of Bone and Joint Surgery, 2007, vol. 89-A (suppl. 3), pp. 144-151.
Kurtz et al., Projections of Primary and Revision Hip and Knee Joint Arthroplasty in the United States, The Journal of Bone and Joint Surgery, 2007, vol. 89-A, No. 4, pp. 780-785.
"Meeting the High Standards of Orthopedic Surgeons", OrthAlign website, http://www.orthalign.com/products_technology/kneealign.asp.
Miki et al., Anatomic Hip Range of Motion After Implantation During Total Hip Arthoroplasty as Measured by a Navigation System, The Journal of Arthroplasty, 2007, vol. 22, No. 7, pp. 946-952.
NaviPro, Kinamed website, http://www.kinamed.com/naviPro.html.
Noble et al., Computer Simulation: How Can it Help the Surgeon Optimize Implant Position?, Clinical Orthopaedics and Related Research, 2003, No. 417, pp. 242-252.
Ong et al., Economic Burden of Revision Hip and Knee Arthroplasty in Medicare Enrollees, Clinical Orthopaedics and Related Research, 2006, No. 446, pp. 22-28.
"ORTHOsoft hip navgation", Zimmer website, http://www.zimmer.com/medical-professionals/our-science/hip/hip-cas.html#1ORTHOsoft.
Renkawitz et al., Principles and New Concepts in Computer-Navigated Total Hip Arthroplasty, Orthopäde, 2011, vol. 40, No. 12, pp. 1095-1102.
Shon et al., Impingement in Total Hip Arthroplasty, The Journal of Arthroplasty, 2005, vol. 20, No. 4, pp. 427-435.
Thornberry et al., The Combined Use of Simulation and Navigation to Demonstrate Hip Kinematics, The Journal of Bone and Joint Surgery, 2009, vol. 91, pp. 144-152.
Usrey et al., Does Neck/Liner Impingement Increase Wear of Ultrahigh-Molecular-Weight Polyethylene Liners?, The Journal of Arthroplasty, 2006, vol. 21, No. 6 (Suppl. 2), pp. 65-71.
"Welcome to the HipSextant" HipSextant website, http://hipsextant.com.
Wines et al., Computed Tomography Measurement of the Accuracy of Component Version in Total Hip Arthroplasty, The Journal of Arthroplasty, 2006, vol. 21, No. 5, pp. 696-701.

* cited by examiner

COMPUTER-GUIDED SYSTEM FOR ORIENTING A PROSTHETIC ACETABULAR CUP IN THE ACETABULUM DURING TOTAL HIP REPLACEMENT SURGERY

REFERENCE TO PENDING PRIOR PATENT APPLICATION

This patent application claims benefit of prior U.S. Provisional Patent Application Ser. No. 61/616,939, filed Mar. 28, 2012 by Robert L. Thornberry for COMPUTER-GUIDED SYSTEM FOR ORIENTING THE ACETABULAR CUP IN THE PELVIS DURING TOTAL HIP REPLACEMENT SURGERY, which patent application is hereby incorporated herein by reference.

FIELD OF THE INVENTION

This invention relates to computer-guided surgery in general, and more particularly to computer-guided surgery for orienting the acetabular cup in the acetabulum during total hip replacement surgery.

BACKGROUND OF THE INVENTION

Joint replacement surgery seeks to replace portions of a joint with prosthetic components so as to provide long-lasting joint function and pain-free mobility for the patient.

Figure 1:
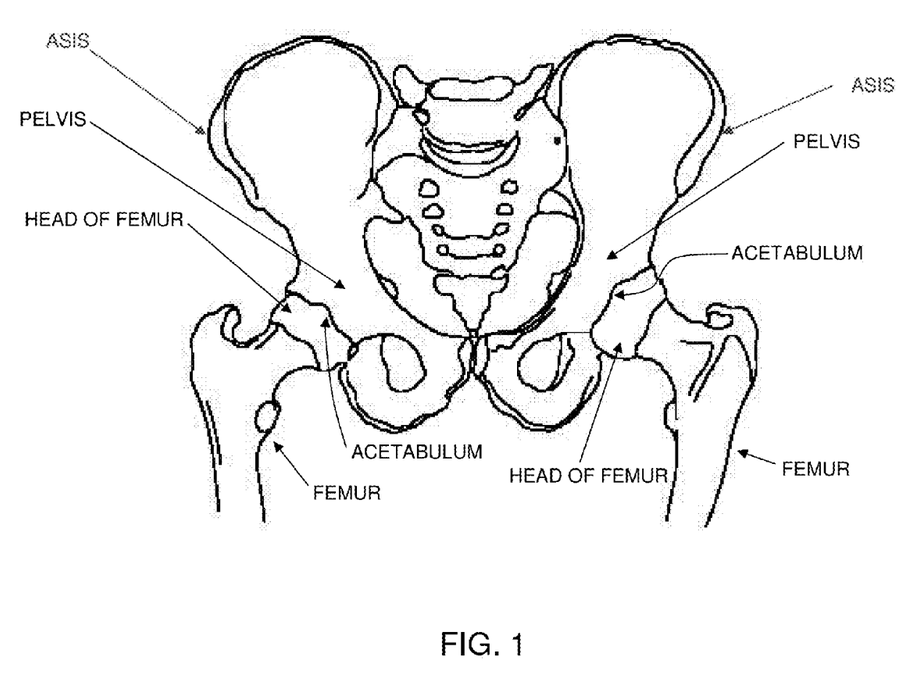
FIG. 1 is a schematic view showing skeletal anatomy in the area of the hip joint.

One joint which is commonly replaced, in whole or in part, is the hip joint. The hip joint is located at the junction of the femur and the acetabulum. More particularly, and looking now at FIG. 1, the head of the femur is received in the acetabulum, with a plurality of ligaments and other soft tissue serving to hold the bones in articulating relation.

Figure 2:
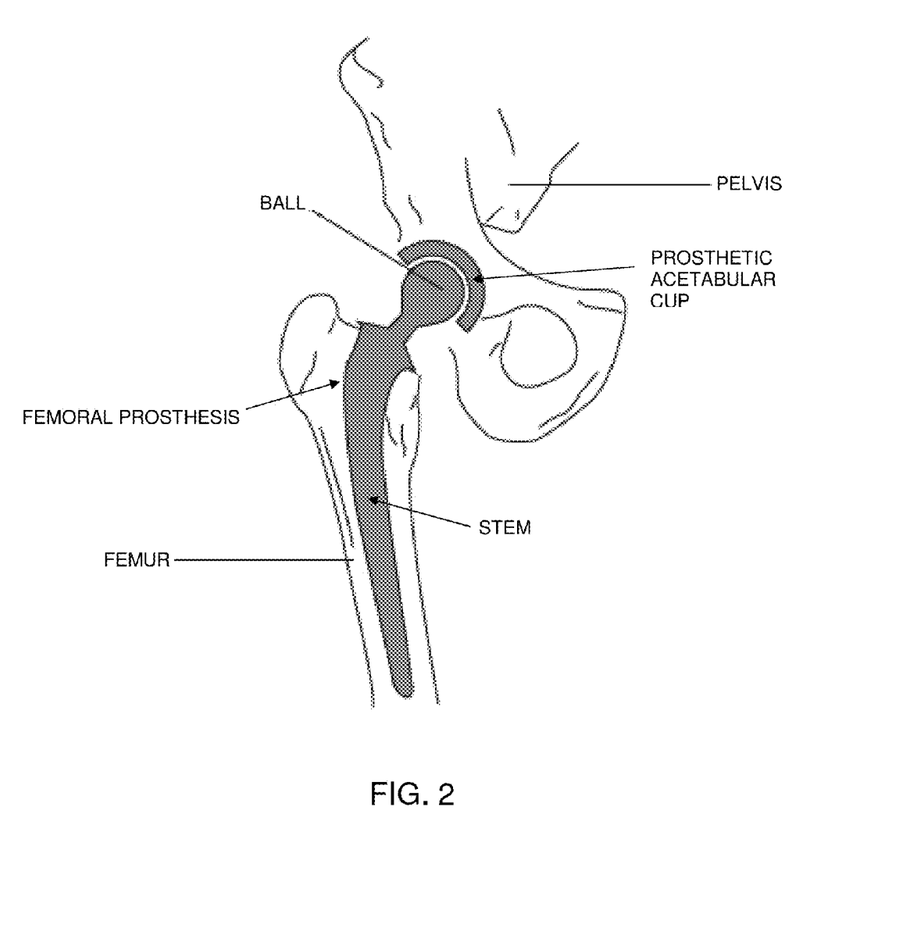
FIG. 2 is a schematic view showing a total hip replacement.

During total hip replacement surgery, and looking now at FIG. 2, the operative elements of the hip joint (i.e., the head of the femur and the acetabular cup) are replaced by prosthetic components. More particularly, during total hip replacement surgery, the head of the femur is replaced by a prosthetic ball-and-stem, and the natural acetabular cup is replaced by a prosthetic acetabular cup, whereby to provide the prosthetic total hip joint.

In a partial hip replacement surgery, only one of the operative elements of the hip joint may be replaced, e.g., the head of the femur.

The present invention will hereinafter be discussed in the context of a total hip replacement surgery, however, it should also be appreciated that the present invention may be equally applicable to a partial hip replacement surgery.

In order to replace the head of the femur with the femoral prosthesis, the head of the femur is first distracted from the acetabulum so as to expose the femoral head. Then an osteotomy is performed on the femoral neck so as to remove the neck and head of the femur from the remainder of the femur. Next, the proximal end of the intramedullary canal is prepared to receive the stem of the femoral prosthesis. More particularly, a rasp, reamer, broach, etc. is used to hollow out, clean and enlarge the intramedullary canal of the femur so as to create a cavity to receive the stem of the femoral prosthesis. Once the proximal end of the intramedullary canal has been prepared to receive the femoral prosthesis, the stem of the femoral prosthesis is inserted into the intramedullary canal so that the ball of the femoral prosthesis is appropriately presented to the acetabular cup. Typically, the ball of the femoral prosthesis is formed separately from the stem of the femoral prosthesis, and it is mounted to the stem of the femoral prosthesis at the time of use.

Furthermore, it should also be appreciated that during the surgery itself, it is common to temporarily position a trial stem or broach in the femur, attach a trial ball or equivalent element to the trial stem or broach, and then temporarily reduce the joint so as to confirm the reconstruction before the actual prosthetic stem is secured in position within the femur.

In order to replace the native acetabular cup with the prosthetic acetabular cup, the native acetabulum is first prepared to receive the prosthetic acetabular cup. This generally involves reaming an appropriate seat in the acetabulum to receive the prosthetic acetabular cup. Then the prosthetic acetabular cup is installed in the seat formed in the acetabulum, and the distraction released, so that the ball of the femoral prosthesis can be seated in the prosthetic acetabular cup. In this respect it will be appreciated that the prosthetic acetabular cup typically comprises an outer cup made of metal and an inner liner made of polyethylene (or another polymer, or a ceramic, or a metal, etc.). The metal outer cup is configured so as to be received in the seat formed in the acetabulum and thereafter osseointegrate into the host bone, and the polyethylene inner liner is configured so as to be received in the metal outer cup and thereafter provide a low-friction seat for the ball of the femoral prosthesis.

During seating of the prosthetic acetabular cup in the acetabulum, it is important that the prosthetic acetabular cup be set in the acetabulum with the proper positioning, i.e., at the proper location and with the proper orientation. Such proper positioning is important in order to (i) avoid impingement between the rim of the prosthetic acetabular cup and the neck of the femoral prosthesis as the prosthetic joint is moved through a range of motions, since such impingement can result in a reduced range of motion, excessive wear, joint failure and/or substantial pain for the patient, and (ii) avoid dislocation of the ball of the femoral prosthesis from the acetabular cup as the joint is moved through a range of motions, since such dislocation can result in damage to the anatomy, joint failure and/or substantial pain for the patient.

In many cases, the surgeon seats the prosthetic acetabular cup in the acetabulum "by eye", and thereafter confirms the proper disposition of the prosthetic acetabular cup when the distracted joint is subsequently reduced. However, this approach relies heavily on the anatomical view available to, and appreciated by, the surgeon, and errors in cup orientation (i.e., tilt) may not be discovered until after the surgery has been completed, since such errors in cup orientation can be difficult to detect interoperatively, even where X-ray imaging is available.

For this reason, various computer-guided systems have been developed to assist the surgeon in the proper placement of the prosthetic acetabular cup during total hip replacement surgery. However, such computer-guided systems frequently require that a CT scan be made of the patient in advance of the procedure so as to determine the geometry of the acetabulum. Furthermore, such computer-guided systems typically require (i) the registration and tracking of pelvic anatomical landmarks (e.g., the pubic tubercles and the anterior/superior iliac spines) prior to and during the surgery, e.g., with optical or electromagnetic trackers placed on the pelvic anatomical landmarks, and (ii) the registration and tracking of femoral anatomical landmarks prior to and during the surgery, e.g., with optical or electromagnetic trackers placed on the femoral anatomical landmarks. However, in practice, one or more of the pelvic anatomical landmarks can be difficult to physically access during the procedure. Furthermore, the optical or electromagnetic trackers must typically be applied to both the pelvic anatomical landmarks and the femoral anatomical landmarks during the surgery itself so as to track the dispositions of these body parts during the surgery. These requirements can add to the cost of the procedure, can lengthen the time required for the procedure, and can be inconvenient for the surgeon (e.g., such as where the surgeon must work around optical trackers protruding into the surgical field). In this respect it should be appreciated that optical trackers, while providing good spatial resolution, suffer from the disadvantage that they must remain directly visible at all times; electromagnetic trackers, while not requiring direct visual access, suffer from the disadvantage of poor spatial resolution.

Accordingly, there is a need for a new and improved computer-guided system for orienting a prosthetic acetabular cup in the acetabulum during total hip replacement surgery, wherein the need for a pre-operative CT scan can be eliminated, and wherein the need to physically access pelvic anatomical landmarks during the procedure can be eliminated.

In addition, there is also a need for a new and improved computer-guided system which can be used to orient prosthetic components other than a prosthetic acetabular cup, e.g., a computer-guided system which can be used to orient a femoral prosthetic component.

Furthermore, there is also a need for a new and improved computer-guided system which can be used to orient prosthetic components for joints other than the hip, e.g., a computer-guided system which can be used to orient prosthetic components in the knee.

And there is a need for a new and improved computer-guided system which can be used to determine and adjust the position of substantially any two interacting components in space.

SUMMARY OF THE INVENTION

The present invention provides a new and improved computer-guided system for orienting a prosthetic acetabular cup in the acetabulum during total hip replacement surgery, wherein the need for a pre-operative CT scan can be eliminated, and wherein the need to physically access pelvic anatomical landmarks during the procedure can be eliminated.

In addition, the present invention provides a new and improved computer-guided system which can be used to orient prosthetic components other than a prosthetic acetabular cup, e.g., a computer-guided system which can be used to orient a femoral prosthetic component.

Furthermore, the present invention provides a new and improved computer-guided system which can be used to orient prosthetic components for joints other than the hip, e.g., a computer-guided system which can be used to orient prosthetic components in the knee.

And the present invention provides a new and improved computer-guided system which can be used to determine and adjust the position of substantially any two interacting components in space.

In one preferred form of the invention, there is provided a computer-guided system for orienting an insert during a surgical procedure, the computer-guided system comprising:
 a surgical table for supporting a patient, the surgical table being capable of movement about three axes;
 a table inertial measurement unit for measuring movement of the surgical table;
 a patient inertial measurement unit for measuring movement of the patient;
 an insert inertial measurement unit for measuring movement of the insert; and
 computational means for determining the relative positioning of the patient and the insert based upon movement of the surgical table, movement of the patient, and movement of the insert.

In another preferred form of the invention, there is provided a method for orienting an insert during a surgical procedure, the method comprising:
 providing a computer-guided system comprising:
  a surgical table for supporting a patient, the surgical table being capable of movement about three axes;
  a table inertial measurement unit for measuring movement of the surgical table;
  a patient inertial measurement unit for measuring movement of the patient;
  an insert inertial measurement unit for measuring movement of the insert; and
  computational means for determining the relative positioning of the patient and the insert based upon movement of the surgical table, movement of the patient, and movement of the insert;
 calibrating the table inertial measurement unit;
 positioning the patient on the surgical table with a known orientation, and zeroing the patient inertial measurement unit;
 moving the table in a known manner, and determining the position of the patient relative to the position of the surgical table;
 positioning the insert on the patient; and
 moving the surgical table in a known manner, and determining the position of the insert relative to the position of the patient.

In another preferred form of the invention, there is provided a computer-guided system for orienting an insert during a surgical procedure, the computer-guided system comprising:
 a surgical table for supporting a patient, the surgical table being capable of movement about three axes;
 an ultrasound device for identifying at least two anatomical landmarks on the patient, the ultrasound device being mounted to one of the patient and the surgical table;
 a first position sensor for measuring the position of the ultrasound device;
 a second position sensor for measuring the position of the insert; and
 computational means for determining the relative positioning of the patient and the insert based upon movement of the surgical table and movement of the insert.

In another preferred form of the invention, there is provided a method for orienting an insert during a surgical procedure, the method comprising:
 providing a computer-guided system comprising:
  a surgical table for supporting a patient, the surgical table being capable of movement about three axes;
  an ultrasound device for identifying at least two anatomical landmarks on the patient;
  a first position sensor for measuring the position of the ultrasound device;
  a second position sensor for measuring the position of the insert; and computational means for determining the relative positioning of the patient and the insert based upon movement of the surgical table and movement of the insert;

mounting the ultrasound device to one of the patient and the surgical table;

positioning the insert on the patient; and moving the surgical table in a known manner, and determining the position of the insert relative to the position of the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 3:
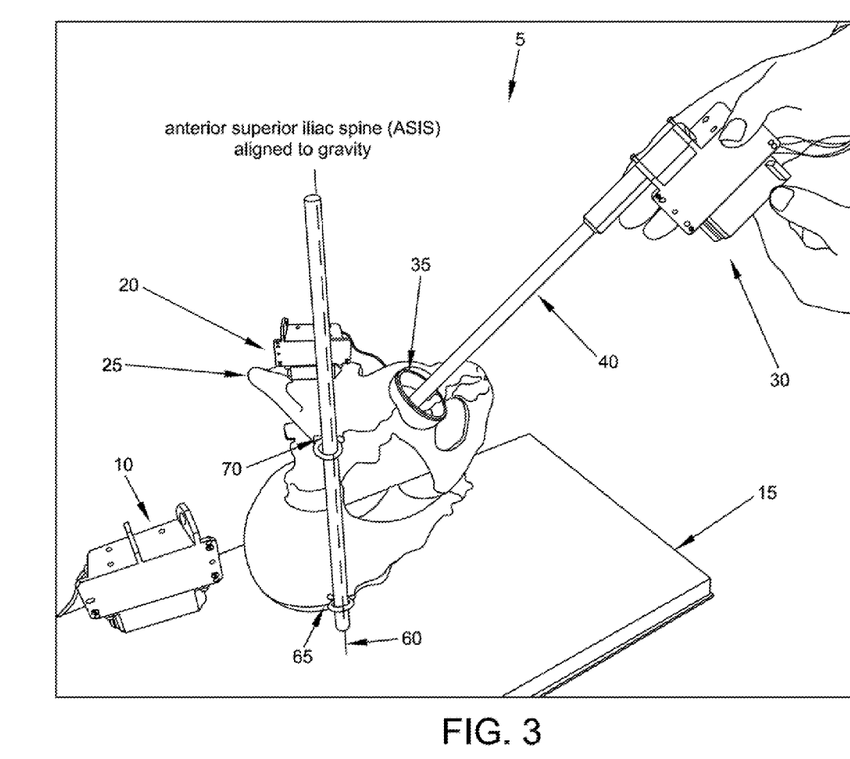
FIGS. 3-5 are schematic views showing a computer-guided system for orientating a prosthetic acetabular cup in the acetabulum during total hip replacement surgery, wherein the computer-guided system comprises inertial measurement units (IMUs) on the surgical table, pelvis of the patient and the insert.
Figure 4:
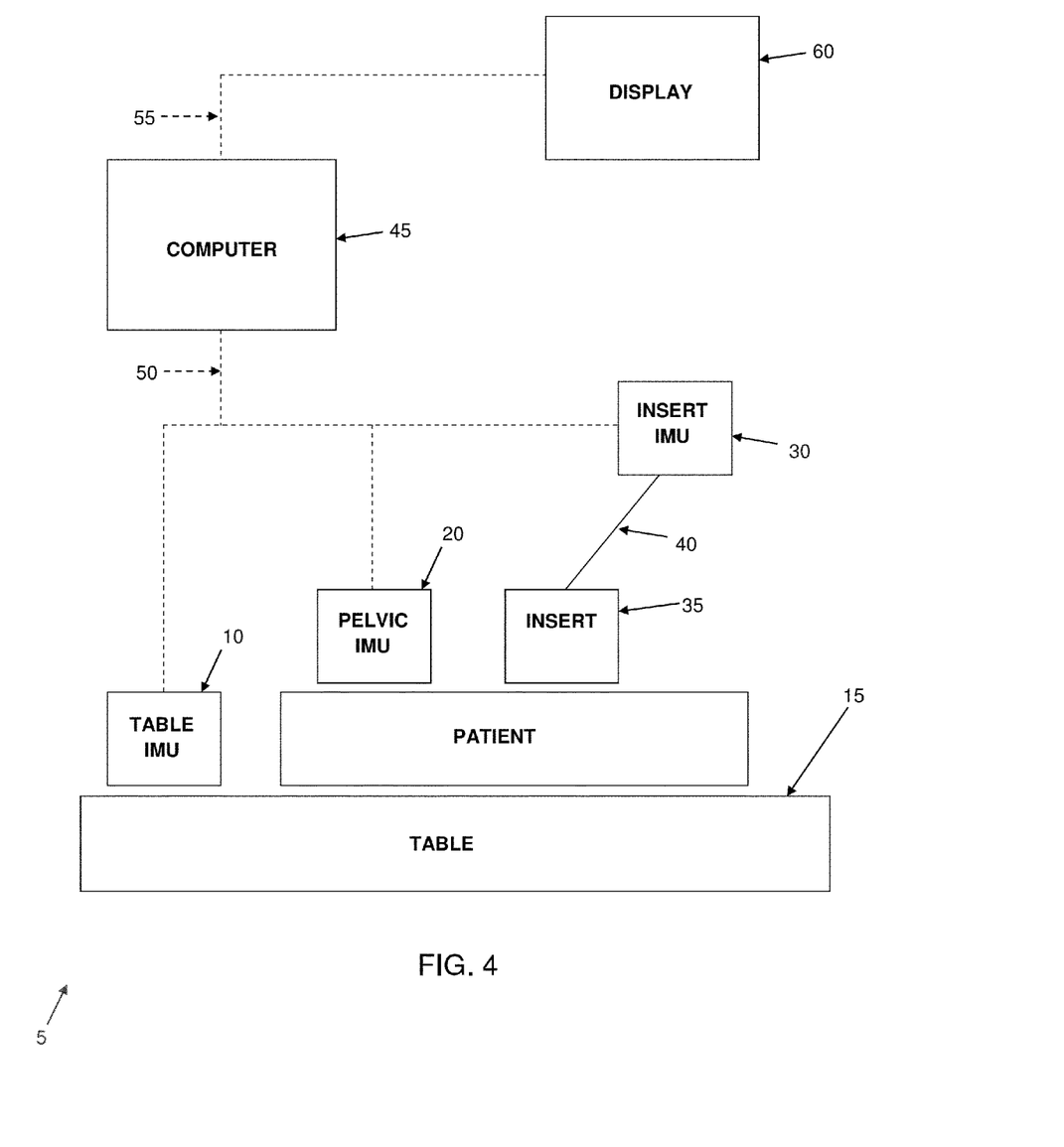
Figure 5:
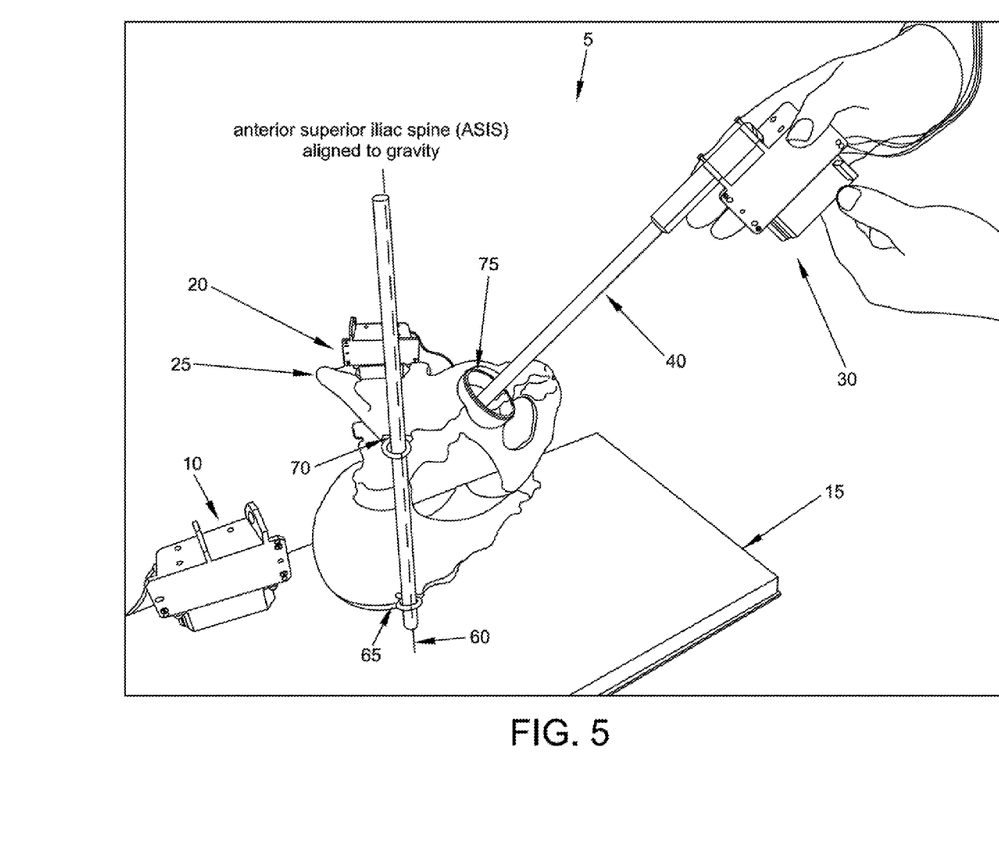

Computer-Guided System Using Inertial Measurement Units (IMUs) on the Surgical Table, Pelvis of the Patient and the Insert for Orienting a Prosthetic Acetabular Cup in the Acetabulum During Total Hip Replacement Surgery In one form of the invention, and looking now at FIGS. 3-5, there is provided a computer-guided system 5 for orienting a prosthetic acetabular cup in the acetabulum during total hip replacement surgery. Computer-guided system 5 generally comprises a table inertial measurement unit (IMU) 10 mounted to a surgical table 15 for measuring movement of the surgical table, wherein the surgical table is capable of movement about three axes (X, Y and Z); a pelvic IMU 20 attached to the pelvis 25 of a patient for measuring movement of the pelvis; and an insert IMU 30 attached to an insert 35 which is to be mounted to the pelvis with a desired positioning, with the insert IMU 30 configured for measuring movement of the insert. By way of example but not limitation, table IMU 10, pelvic IMU 20 and/or insert IMU 30 comprise any appropriate electronic device that measures and reports on the movement of an object using a combination of accelerometers and gyroscopes and/optionally magnetometers. By way of further example but not limitation, insert 35 may comprise a prosthetic acetabular cup which is to be mounted to the acetabulum of the patient, and insert IMU 30 may be attached to a handle 40 which is attached to insert 35. Computer-guided system 5 also comprises computational means 45 (e.g., an appropriately programmed general purpose computer), input means 50 for acquiring data from the aforementioned table IMU 10, pelvic IMU 20 and insert IMU 30 and transmitting the same to computational means 45, and output means 55 for transmitting data from computational means 45 to a display 60 for displaying information from computational means 45 to the user, whereby to provide computer guidance to the user when positioning insert 35 relative to the pelvis 25 of the patient.

Computer-guided system 5 is preferably operated as follows.

1. Table IMU 10 is attached to surgical table 15 and calibrated.

2. The patient is positioned on surgical table 15 with the patient lying on their side. Pelvic IMU 20 is attached to pelvis 25 of the patient, e.g., with pins (not shown) extending into the pelvis. Pelvic IMU 20 can be attached to pelvis 25 at substantially any location on the pelvis, but is preferably attached to the pelvis at an "out-of-the-way" location so as to avoid interfering with the surgical process.

3. The patient is then manipulated on surgical table 15 so that an imaginary line 60 connecting the two Anterior Superior Iliac Spine points 65, 70 (i.e., the ASIS-ASIS line) is parallel to the line of gravity and perpendicular to the horizon (i.e., so that the patient is in the "lateral position"). Pelvic IMU 20 is then "zeroed". Alternatively, the patient could be manipulated so that the ASIS-ASIS line is parallel to the horizon, i.e., so that the patient is in the "supine position".

4. At this point, surgical table 15 is moved in a known manner (e.g., by moving the table successively in each of the X, Y and Z axes), and the movement of table IMU 10 and pelvic IMU 20 is identified so that the position of pelvis 25 can be determined vis-à-vis surgical table 15. In other words, table IMU 10 is secured to the table and calibrated, pelvic IMU 20 is secured to the pelvis, the pelvis is put in a known position (i.e., with the ASIS-ASIS line set vertical) and pelvic IMU 20 is zeroed, and then the surgical table is moved in a known manner—then, by monitoring the data from pelvic IMU 20 and table IMU 10, the position of the pelvis can be determined relative to the position of the table. Note that this is done using inertial measurement units (table IMU 10 and pelvic IMU 20) and does not require the use of any optical or electromagnetic trackers.

5. The patient is then prepared and draped for total hip arthroplasty, with pelvic IMU 20 being located under the sterile drape. Note that locating pelvic IMU 20 under the sterile drape does not present an issue, since it is an inertial measurement unit and does not require optical tracking.

6. The hip joint is then exposed in the normal surgical manner.

7. Next, and prior to dislocation of the hip joint, the leg length is measured, and the offset of the hip is measured from the center of rotation of the acetabular cup, using any of the various measures well known in the art, e.g., with mechanical guides, with or without sensors, etc.

8. The hip joint is dislocated.

9. Note that any movement of the patient on the surgical table during Steps 5-8 is identified by virtue of movement of pelvic IMU 20 (moved) vis-à-vis table IMU 10 (not moved).

In other words, any movement of the anatomy during Steps 5-8 can be identified by comparing the data from pelvic IMU 20 (which may have moved) vis-à-vis table IMU 10 (which has not moved). Thus, even though the anatomy moves during Steps 5-8, the position of the anatomy is still known by virtue of the data from pelvic IMU 20 and table IMU 10.

10. The center of rotation of the hip is then identified by inserting an acetabular sizer/reamer/impactor (inserter) 75 (with insert IMU 30 attached to the handle 40 of the sizer/reamer/impactor (inserter)) into the natural acetabular cup and fixing the sizer/reamer/impactor (inserter) in position. See FIG. 5. This can typically be done with appropriate accuracy by eye. Insert IMU 30 is calibrated for this position. In other words, insert IMU 30 is zeroed when it is located at the center of rotation of the hip.

11. Next, the surgical table is moved, which causes the patient to be moved, which causes the insert to be moved. More particularly, surgical table 15 is moved relative to the X, Y, Z axes, which movement is identified via table IMU 10. At the same time, the movement of pelvis 25 (induced by movement of surgical table 15) is identified via pelvic IMU 20, and the movement of the acetabular sizer/reamer/impactor (inserter) 75 (also induced by the table movement) is identified by insert IMU 30. Significantly, the kinematic data acquired by table IMU 10, pelvic IMU 20 and insert IMU 30 allows the orientation of the acetabular sizer/reamer/impactor (inserter) to be determined relative to the pelvis, and hence allows pelvic flexion and extension to be determined.

12. The acetabulum is then reamed using acetabular sizer/reamer/impactor (inserter) 75, with insert IMU 30 being used to guide the depth and direction of reaming.

13. Insert 35 (i.e., the prosthetic acetabular cup) is then positioned in the acetabulum using handle 40 of the acetabular sizer/reamer/impactor (inserter)) to manipulate the acetabular cup into position, with insert IMU 30 being used to guide proper positioning of the insert (i.e., the prosthetic acetabular cup) in the acetabulum. See FIG. 3. In this respect it will be appreciated that, if desired, surgical table 15 can be cycled through its aforementioned movements relative to the X, Y, Z axes so as to confirm component positioning (i.e., the surgical table is moved relative to the X, Y, Z axes, which causes movement of the pelvis relative to the X, Y, Z axes, and movement of the cup inserter relative to the X, Y, Z axes, with table movement being identified by table IMU 10, pelvic movement being identified by pelvic IMU 20, and with cup movement being identified by insert IMU 30, such that the kinematic data acquired by the table IMU, the pelvic IMU and the insert IMU allows the orientation of the insert (i.e., the acetabular cup) to be determined relative to the pelvis, and the location of the insert can be determined using the various measures discussed in Step 7 above.

14. After the insert (i.e., the prosthetic acetabular cup) has been appropriately positioned using computer-guided system 5, handle 40 (with insert IMU 30 attached) is removed.

15. The trial liner is placed in the acetabular shell.

16. Surgery is completed by broaching the femur, doing trial reduction with the broach and head and neck trials, and checking leg length/offset using tools for measurement such as those identified in Step 7, before placing final implants in the patient.

17. The final implants (acetabular liner, femoral stem and femoral head) are placed in the patient.

18. The pelvic IMU 20 is removed from the patient.

19. The surgical wounds are closed and dressings placed.

In the foregoing description, computer-guided system 5 has been described in the context of orienting a prosthetic acetabular cup in the acetabulum during total hip replacement surgery. However, it should be appreciated that computer-guided system 5 may be used to orient another prosthetic component during total hip replacement surgery (e.g., a femoral stem). Or computer-guided system 5 may be used to orient another component during another reconstruction surgery (e.g., a humeral head during proximal humerus reconstruction, etc.).

System Using Ultrasound to Identify the Position and Orientation of the Pelvis In another form of the invention, computer-guided system 5 is configured to use ultrasound to identify the position and orientation of the pelvis.

Figure 6:
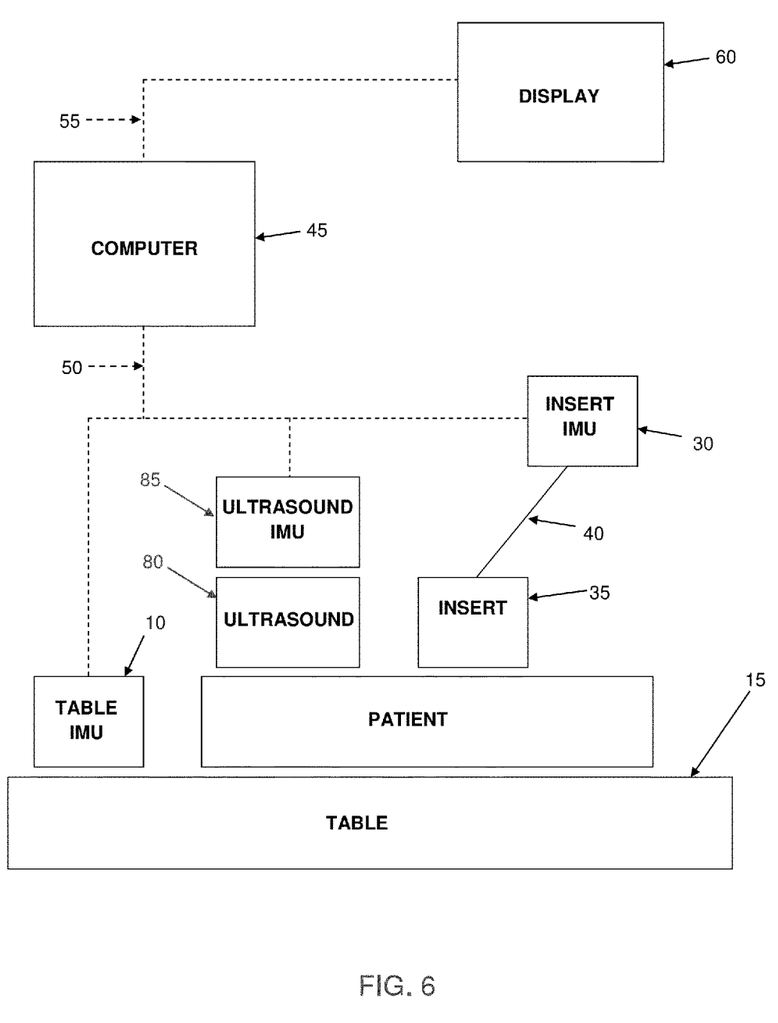
FIG. 6 is a schematic view showing a computer-guided system for orientating a prosthetic acetabular cup in the acetabulum during total hip replacement surgery, wherein the computer-guided system comprises an ultrasound device and inertial measurement units (IMUs) on the surgical table, ultrasound device and the insert.

More particularly, in another form of the invention, and looking now at FIG. 6, pelvic IMU 20 is eliminated from the system, and an ultrasound device 80 and an ultrasound IMU 85 is provided for the system. Ultrasound device 80 is clamped to the pelvis using a pelvic clamping device (e.g., one similar to the Stulberg Positioner) so that the ultrasound head(s) of ultrasound device 80 is (are) directed at the ASIS point(s) of the patient. As a result, using ultrasound device 80 to identify the position of the pelvis (by identifying the two ASIS points of the pelvis), and using ultrasound IMU 85 to identify movement of ultrasound device 80 (and hence movement of pelvis 25), computer-guided system 5 can again be used to orient a prosthetic acetabular cup in the acetabulum during total hip replacement surgery.

In essence, with this form of the invention, after table IMU 10 has been calibrated and ultrasound device 80 has identified the two ASIS points of the patient, surgical table 15 is moved in a known manner, and the movement of table IMU 10 and ultrasound IMU 85 is identified so that the position of pelvis 25 can be determined vis-à-vis surgical table 15. Then the center of rotation of the hip is identified by inserting an acetabular sizer/reamer/impactor (inserter) 75 (with insert IMU 30 attached to handle 40 of the sizer/reamer/impactor (inserter)) into the natural acetabular cup of the patient and fixing the sizer/reamer/impactor (inserter) in position at that center of rotation, and then the insert IMU 30 is zeroed. Then surgical table 15 is moved in a known manner, which causes pelvis 25 to move, and acetabular sizer/reamer/impactor (inserter) 75 to move. As this occurs, table IMU 10, ultrasound IMU 85 and insert IMU 30 provide the data necessary to determine the orientation of the acetabular sizer/reamer/impactor (inserter) relative to the pelvis, and hence allows pelvic flexion and tension to be determined. Subsequently, insert 35 is positioned in the acetabulum using handle 40, with surgical table 15 being cycled through its movements as necessary, so as to allow the orientation of the insert (i.e., the acetabular cup) to be determined relative to the pelvis, again using table IMU 10, ultrasound IMU 85 and insert IMU 30, and the location of the insert can be determined using the various measures discussed in Step 7 above.

Figure 7:
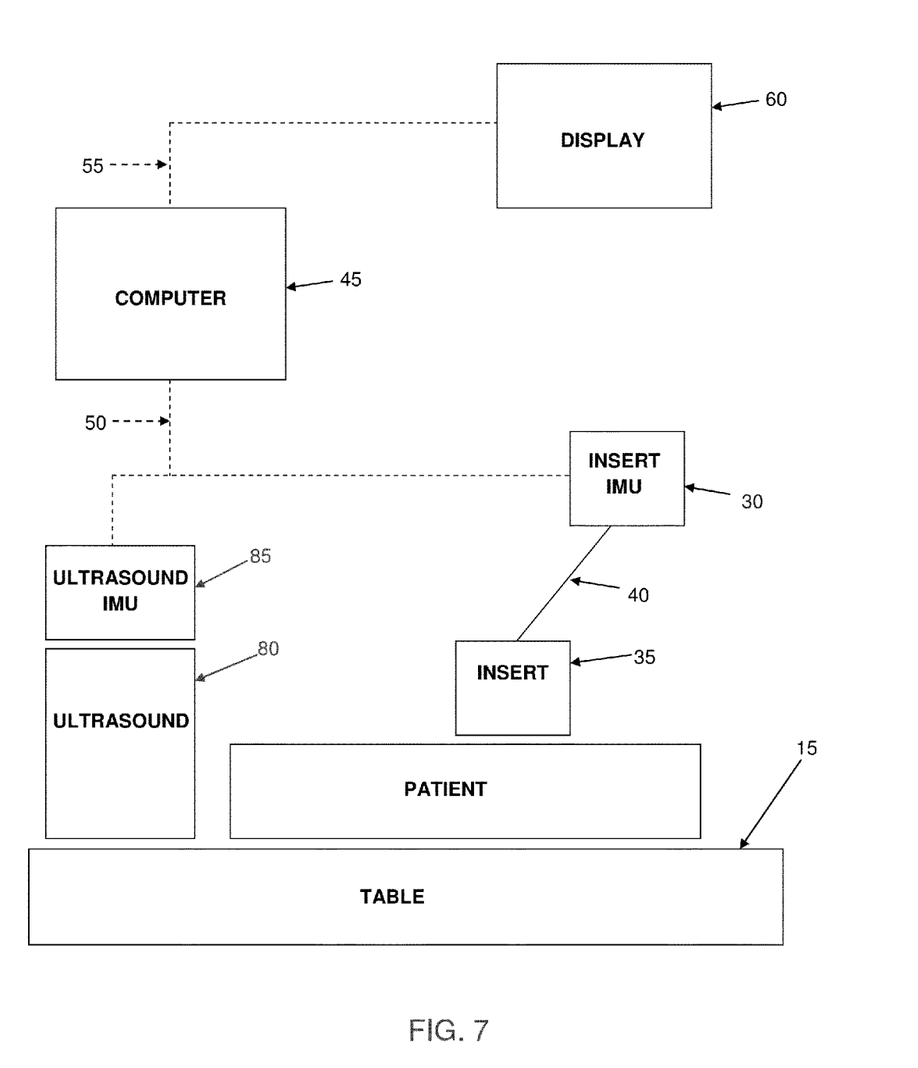
FIG. 7 is a schematic view showing a computer-guided system for orientating a prosthetic acetabular cup in the acetabulum during total hip replacement surgery, wherein the computer-guided system comprises an ultrasound device mounted to the surgical table and inertial measurement units (IMUs) on the ultrasound device and the insert.

In still another form of the invention, and looking now at FIG. 7, table IMU 10 and pelvic IMU 20 are eliminated from the system, and the ultrasound device 80 and the ultrasound IMU 85 are provided for the system. Ultrasound device 80 is clamped to the surgical table 15 so that the ultrasound head(s) of ultrasound device 80 is (are) directed at the two ASIS points of the patient. As a result, using ultrasound device 80 to identify the position of the pelvis (by identifying the two ASIS points of the pelvis), and using ultrasound IMU 85 to identify movement of surgical table 15 and pelvis 25, computer-guided system 5 can again be used to orient a prosthetic acetabular cup in the acetabulum during total hip replacement surgery.

In essence, with this form of the invention, ultrasound device 80 identifies the two ASIS points of the patient and the position of pelvis 25 vis-à-vis surgical table 15. Then the center of rotation of the hip is identified by inserting an acetabular sizer/reamer/impactor (inserter) 75 (with insert IMU 30 attached to handle 40 of the sizer/reamer/impactor (inserter)) into the natural acetabular cup of the patient and fixing the sizer/reamer/impactor (inserter) in position at that center of rotation, and then the insert IMU 30 is zeroed. Then surgical table 15 is moved in a known manner, which causes pelvis 25 to move, and acetabular sizer/reamer/impactor (inserter) 75 to move. As this occurs, ultrasound IMU 85 and insert IMU 30 provide the data necessary to determine the orientation of the acetabular sizer/reamer/impactor (inserter) relative to the pelvis, and hence allows pelvic flexion and tension to be determined. Subsequently, insert 35 is positioned in the acetabulum using handle 40, with surgical table 15 being cycled through its movements as necessary, so as to allow the orientation of the insert (i.e., the acetabular cup) to be determined relative to the pelvis, again using ultrasound IMU 85 and insert IMU 30, and the location of the insert can be determined using the various measures discussed in Step 7 above.

System Using Other Sensors in Place of IMUs

If desired, computer-guided system 5 may use other sensors in place of the IMUs discussed above (i.e., in place of table IMU 10, pelvic IMU 20, insert IMU 30 and ultrasound IMU 85). These sensors may comprise other position and/or movement and/or motion sensors capable of determining orientation and/or motion, e.g., accelerometers, gyroscopes, magnetometers, tilt sensors and/or combinations of the foregoing.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A computer-guided system for orienting an insert in a joint of a patient during a surgical procedure, the computer-guided system comprising:
   a surgical table for supporting a patient, the surgical table being capable of movement about three axes;
   an ultrasound device for identifying at least two anatomical landmarks in a joint of the patient, the ultrasound device configured to be mounted to one of the patient and the surgical table, with the ultrasound device configured to be directed at two anatomical landmarks in the joint of the patient;
   a first position sensor mounted to the ultrasound device for measuring movement of the ultrasound device;
   a second position sensor mounted to the insert for measuring movement of the insert in the joint of the patient; and
   computational means for determining the position of the insert relative to the joint of the patient based upon data obtained by the first position sensor and the second position sensor during movement of the surgical table, ultrasound device, and insert without pre-operative CT scanning.

2. A computer-guided system according to claim 1 wherein the ultrasound device is configured to be mounted to the patient.

3. A computer-guided system according to claim 1 wherein the ultrasound device is mounted to the surgical table.

4. A computer-guided system according to claim 1 wherein the first position sensor comprises a device capable of determining at least one of orientation and motion.

5. A computer-guided system according to claim 4 wherein the first position sensor comprises an inertial measurement unit.

6. A computer-guided system according to claim 1 wherein the second position sensor comprises a device capable of determining at least one of orientation and motion.

7. A computer-guided system according to claim 6 wherein the second position sensor comprises an inertial measurement unit.

8. A computer-guided system according to claim 1 wherein the at least two anatomical landmarks on the patient comprise two Anterior Superior Iliac Spine (ASIS) points.

9. A computer-guided system according to claim 1 wherein the insert comprises a prosthetic acetabular cup.

10. A computer-guided system according to claim 1 wherein the computer-guided system further comprises a third position sensor mounted to the surgical table for measuring movement of the surgical table.

11. A method for orienting an insert in a joint of a patient during a surgical procedure, the method comprising:
    providing a computer-guided system comprising:
      a surgical table for supporting a patient, the surgical table being capable of movement about three axes;
      an ultrasound device for identifying at least two anatomical landmarks in a joint of the patient;
      a first position sensor mounted to the ultrasound device for measuring movement of the ultrasound device;
      a second position sensor mounted to the insert for measuring movement of the insert in the joint of the patient; and
      computational means for determining the position of the insert relative to the joint of the patient based upon data obtained by the first position sensor and the second position sensor during movement of the surgical table, ultrasound device, and insert without pre-operative CT scanning;
    mounting the ultrasound device to one of the patient on the surgical table and the surgical table, with the ultrasound device directed at two anatomical landmarks in the joint of the patient;
    positioning the insert in the joint of the patient; and
    moving the surgical table so as to cause the insert in the joint of the patient to move, and determining the position of the insert relative to the joint of the patient, wherein the position of the insert is determined from data obtained by the first position sensor and the second position sensor during movement of the surgical table, ultrasound device and insert.

12. A method according to claim 11 wherein the ultrasound device is mounted to the patient.

13. A method according to claim 11 wherein the ultrasound device is mounted to the surgical table.

14. A method according to claim 11 wherein the first position sensor comprises a device capable of determining at least one of orientation and motion.

15. A method according to claim 14 wherein the first position sensor comprises an inertial measurement unit.

16. A method according to claim 11 wherein the second position sensor comprises a device capable of determining at least one of orientation and motion.

17. A method according to claim 16 wherein the second position sensor comprises an inertial measurement unit.

18. A method according to claim 11 wherein the at least two anatomical landmarks on the patient comprise two Anterior Superior Iliac Spine (ASIS) points.

19. A method according to claim 11 wherein the insert comprises a prosthetic acetabular cup.

20. A method according to claim 11 wherein the computer-guided system further comprises a third position sensor mounted to the surgical table for measuring movement of the surgical table.

* * * * *